(12) United States Patent
Schembre et al.

(10) Patent No.: US 9,986,981 B2
(45) Date of Patent: *Jun. 5, 2018

(54) ENDOSCOPIC ULTRASOUND-GUIDED NOTCHED BIOPSY NEEDLE

(71) Applicant: Cook Medical Technologies LLC, Bloomington, IN (US)

(72) Inventors: Drew B. Schembre, Seattle, WA (US); Michael S. Clancy, Limerick (IE); Kevin Chmura, Lewisville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/703,146

(22) Filed: May 4, 2015

(65) Prior Publication Data

US 2015/0230780 A1 Aug. 20, 2015

Related U.S. Application Data

(63) Continuation of application No. 13/079,226, filed on Apr. 4, 2011.

(Continued)

(51) Int. Cl.
| | | |
|---|---|---|
| *A61B 10/02* | (2006.01) | |
| *A61B 10/04* | (2006.01) | |
| *A61B 8/08* | (2006.01) | |
| *A61B 1/018* | (2006.01) | |
| *A61B 1/24* | (2006.01) | |

(52) U.S. Cl.
CPC ......... *A61B 10/0275* (2013.01); *A61B 1/018* (2013.01); *A61B 1/24* (2013.01); *A61B 8/0841* (2013.01); *A61B 8/481* (2013.01); *A61B 10/04* (2013.01); *A61B 2010/045* (2013.01)

(58) Field of Classification Search
CPC ............... A61B 10/0275; A61B 10/04; A61B 2017/3413; A61B 2010/045; A61B 2010/0093
USPC .......... 600/562–572; 604/272, 274; 606/167, 606/170–171, 180
See application file for complete search history.

(56) References Cited

U.S. PATENT DOCUMENTS 4,055,167 A 10/1977 Bernstein
4,249,541 A * 2/1981 Pratt .................. A61B 10/0283
600/566

(Continued)

FOREIGN PATENT DOCUMENTS

CN 2449657 Y 9/2001
WO WO 03/079907 A1 10/2003

OTHER PUBLICATIONS

Chhieng, David C. et al., "Fine-Needle Aspiration Cytology of Hodgkin Disease," Cancer Cytopathology, 2001, American Cancer Society, pp. 52-59.

(Continued)

*Primary Examiner* — Rene Towa
(74) *Attorney, Agent, or Firm* — Brinks Gilson & Lione

(57) ABSTRACT

A notched tissue-collection needle configured similarly to a fine-needle-aspiration needle is provided with a cutting edge disposed in the notch and configured to excise tissue into the notch for collection. A stylet may be provided through a lumen of the needle during introduction into a patient body. The needle may be provided with echogenicity-enhancing features.

17 Claims, 3 Drawing Sheets

Related U.S. Application Data

(60) Provisional application No. 61/321,243, filed on Apr. 6, 2010.

(56) References Cited

U.S. PATENT DOCUMENTS

| | | | |
|---|---|---|---|
| 4,627,444 | A | 12/1986 | Brooker |
| 4,702,260 | A | 10/1987 | Wang |
| 4,791,937 | A | 12/1988 | Wang |
| 4,900,300 | A | 2/1990 | Lee |
| 4,903,709 | A | 2/1990 | Skinner |
| 4,989,614 | A | 2/1991 | Dejter, Jr. et al. |
| 4,991,592 | A | 2/1991 | Christ |
| 5,090,419 | A | 2/1992 | Palestrant |
| 5,106,364 | A | 4/1992 | Hayafuji et al. |
| 5,199,441 | A | 4/1993 | Hogle |
| 5,320,110 | A | 6/1994 | Wang |
| 5,394,887 | A * | 3/1995 | Haaga ............... A61B 10/0275 600/562 |
| 5,449,001 | A | 9/1995 | Terwilliger |
| 5,458,112 | A | 10/1995 | Weaver |
| 5,470,308 | A | 11/1995 | Edwards et al. |
| 5,807,304 | A | 9/1998 | Cockburn |
| 5,817,033 | A | 10/1998 | DeSantis et al. |
| 5,830,153 | A | 11/1998 | Kass |
| 5,865,765 | A | 2/1999 | Mohajer |
| 5,971,939 | A | 10/1999 | DeSantis et al. |
| 6,709,408 | B2 | 3/2004 | Fisher |
| 2003/0083684 | A1 | 5/2003 | Cesarini et al. |
| 2003/0236471 | A1 | 12/2003 | Fisher |
| 2004/0097887 | A1 * | 5/2004 | Secrest ............... A61B 1/00098 604/263 |
| 2005/0070818 | A1 * | 3/2005 | Mueller, Jr. ................ 600/564 |
| 2005/0090765 | A1 | 4/2005 | Fisher |
| 2005/0101879 | A1 | 5/2005 | Shidham et al. |
| 2006/0189891 | A1 | 8/2006 | Waxman et al. |
| 2007/0265647 | A1 | 11/2007 | Bonnette et al. |
| 2008/0091196 | A1 * | 4/2008 | Deal ................ A61B 18/1477 606/45 |
| 2008/0097347 | A1 * | 4/2008 | Arvanaghi ................... 604/264 |
| 2009/0118641 | A1 | 5/2009 | Van Dam et al. |
| 2010/0249750 | A1 * | 9/2010 | Racz ................ A61B 17/3478 604/512 |
| 2011/0098596 | A1 | 4/2011 | Ozturk et al. |
| 2011/0190660 | A1 | 8/2011 | Levy |

OTHER PUBLICATIONS

Davenport, R.D., "Rapid on-site evaluation of transbronchial aspirates," Chest, 1990, vol. 98, pp. 59-61.

Diette, Gregory B. et al., "Utility of On-Site Cytopathology Assessment for Bronchoscopic Evaluation of Lung Masses and Adenopathy," Chest, 2000, vol. 117, pp. 1186-1190.

Gittlen, S.D. et al., "A new versatile transbronchial cytology needle for the staging and diagnosis of bronchogenic carcinoma," Chest, 1988, vol. 94, pp. 561-565.

International Preliminary Report on Patentability and Written Opinion in International Application No. PCT/US2011/031048, dated Oct. 18, 2012, 13 pages.

Kaffes, Arthur J. et al., "Fine Needle Aspiration At Endoscopic Ultrasound With a Novel Olympus Side-Port Needle: A Pilot Experience," Gastrointestinal Endoscopy, Abstract T1492, 2010, vol. 71, No. 5, p. 291.

Mayall, Frederick et al., "Improved FNA cytology results with a near patient diagnosis service for non-breast lesions," J. Clin. Pathol., 1998, vol. 51, pp. 541-544.

Mazzone MD, Peter et al., "Bronchoscopy and Needle Biopsy Techniques for Diagnosis and Staging of Lung Cancer," Clinics in Chest Medicine, vol. 23, No. 1, Mar. 2002, pp. 137-158.

McLoud MD, Theresa C., "Should Cutting Needles Replace Needle Aspiration of Lung Lesions?", Radiology, Jun. 1998, pp. 569-570.

Olympus KeyMed, Diagnosis (Needle Aspiration), obtained from internent address <http://keymed.co.uk/index.cfm/page/.../615>, 2010, 2 pages.

Shure, D., "Transbronchial biopsy and needle aspiration," Chest, 1989, vol. 95, pp. 1130-1138.

Wang, K.P., "Flexible transbronchial needle aspiration biopsy for histologic specimens," Chest, 1985, vol. 88, pp. 860-863.

Wang, Ko Pen, "Biopsy Sampling Techniques," Chest, 1989, vol. 95, pp. 484-485.

Wang, K.P. et al., "Needle brush in the diagnosis of lung mass or nodule through flexible bronchoscopy," Chest, 1991, vol. 100, pp. 1148-1150.

Weisbrod, MD, FRCP, Gordon L. et al., "Preliminary Experience with a Dual Cutting Edge Needle in Thoracic Percutaneous Fine-Needle Aspiration Biopsy," Radiology, Apr. 1987, pp. 75-78.

Yang, Grace, C.H. et al., "Ultrasound-Guided Fine-Needle Aspiration of the Thyroid Assessed by Ultrafast Papanicolaou Stain: Data from 1135 Biopsies with a Two- to Six-Year Follow-Up," Thyroid, vol. 11, No. 6, 2001, pp. 581-589.

* cited by examiner

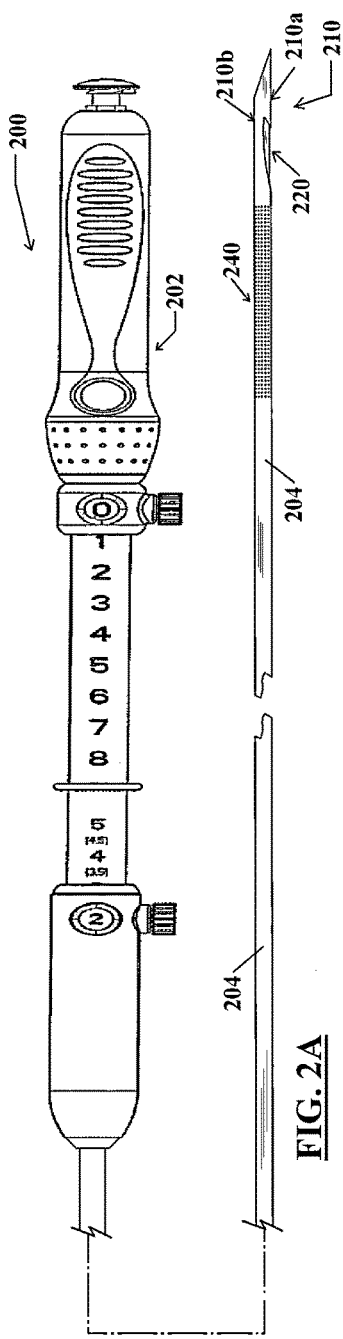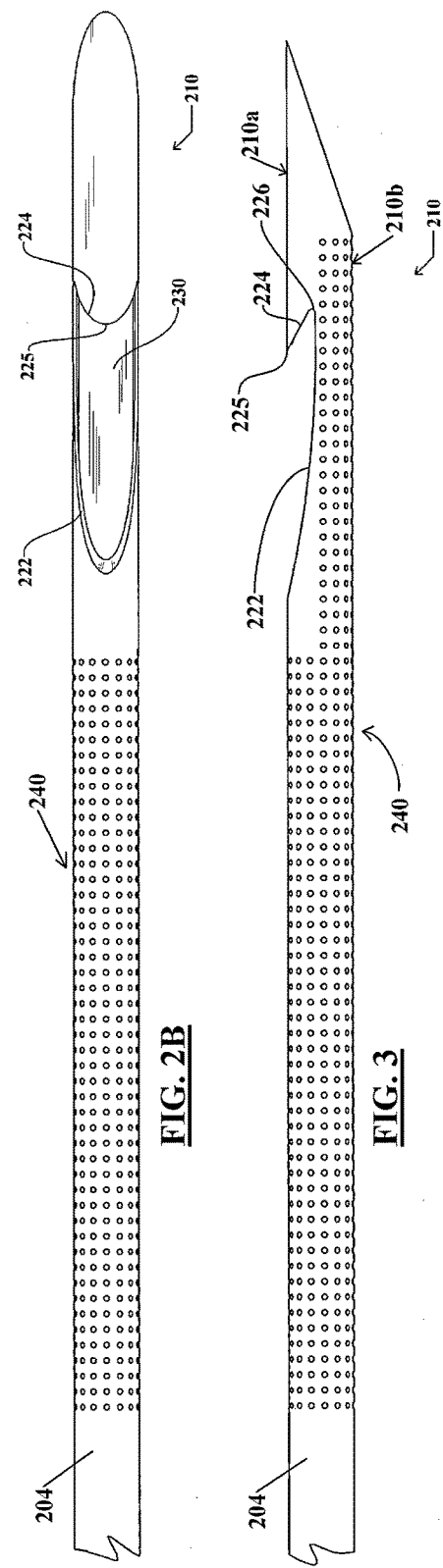
FIG. 2A
FIG. 2B
FIG. 3

ENDOSCOPIC ULTRASOUND-GUIDED NOTCHED BIOPSY NEEDLE

CROSS-REFERENCE TO RELATED APPLICATIONS

This application claims priority as a Continuation under 35 USC § 120 to U.S. patent application Ser. No. 13/079,226, filed Apr. 4, 2011, which claims the benefit of U.S. Provisional Patent Application Ser. No. 61/321,243, filed Apr. 6, 2010, each of which is incorporated herein by reference in its entirety.

TECHNICAL FIELD

The invention relates generally to endoscopic surgical devices. More particularly, the invention pertains to a biopsy needle configured for use during minimally-invasive procedures such as endoscopic procedures.

BACKGROUND

Fine needle aspiration (FNA) is a diagnostic biopsy procedure used to obtain a sample from a target site in a patient body. A fine needle (e.g., 19-gauge to 25-gauge) is directed to a target site, and suction is applied to the proximal end of a lumen of the needle to aspirate cells through its distal end. The procedure typically is far less invasive than other biopsy techniques, whether performed percutaneously (e.g., to sample a suspected breast tumor or subcutaneous lesion) or endoscopically (e.g., to sample a suspected cholangiocarcinoma via a duodenoscope). Moreover, advances in endoscopic ultrasound (EUS) technology have helped physicians and patients by providing enhanced ability of a physician to visualize a biopsy needle to obtain a sample of material from a target site without requiring an open incision or use of large-bore needles and/or laparoscopic trocars.

Current FNA techniques typically obtain only a small number of cells useful for diagnostic evaluation. As a result, this technique includes a risk of false negatives where the few cells obtained in a sample do not accurately represent the presence of a tumor or other disease condition. The small sample size may also limit the diagnostic value of the procedure if the cells obtained are sufficiently few in number or sufficiently damaged during collection that they do not enable a definitive diagnosis. Accordingly it would be advantageous to provide a needle useful for EUS and/or percutaneous FNB (fine needle biopsy) that can obtain a larger sample size (e.g., a larger number of cells in the sample or a "core" comprising intact adjacent cells held together in similar form to their native location) without requiring a larger-gauge needle or requiring multiple passes of the needle to reliably obtain a diagnostically efficacious sample with regard to the number and integrity of the cells in the sample.

BRIEF SUMMARY

Embodiments of needles disclosed here address these problems of the current technology and present advantages over existing needles with regard to both structure and methods. In one aspect a tissue-sampling needle device may include an elongate tubular cannula with a cannula wall defining a cannula lumen, where the cannula lumen extends longitudinally through the cannula. The cannula may include a distal beveled end with a long side and a short side and a notch through the cannula wall that is open to the cannula lumen. The notch is disposed proximally adjacent to the beveled distal cannula end and is generally centered in longitudinal alignment with the long beveled end side and opposite the short beveled end side. Also, the notch may include a distal lip defined by a portion of the cannula wall, the distal lip being configured to extend proximally from a distal-most end of the notch such that a central distal lip portion is disposed proximal of lip end portions that are continuous with generally longitudinal lateral sides of the notch, and to include a proximal-facing cutting edge.

In another aspect, a notched aspiration biopsy needle disclosed herein may include a flexible elongate tubular cannula sized no larger than 19-gauge, with a cannula wall defining a cannula lumen configured to communicate with a proximal source of suction. The cannula lumen extends longitudinally through the cannula, a distal beveled end of the cannula including a long side and a short side, and the structure includes a notch through the cannula wall, open to the cannula lumen. The notch is disposed proximally adjacent to the beveled distal cannula end and is generally centered in longitudinal alignment with the long beveled end side and opposite the short beveled end side, and the notch includes a cutting edge defined by a proximal-facing portion of the cannula wall.

In another aspect, a method of tissue collection may include providing an elongate needle, that includes a beveled distal end and a notch open into a needle lumen, wherein the notch is near the distal end and is disposed opposite an angled distal face of the beveled distal end, and wherein a distal lip defining a distal end portion of the notch comprises a proximally-facing cutting edge. The method may further include directing the distal end of the needle into a target site, applying suction to the needle lumen; and moving the needle proximally in a manner engaging the proximally-facing cutting edge with the target site such that a sample from the target site is collected into the needle lumen.

BRIEF DESCRIPTION OF THE DRAWINGS

In order to assist the understanding of embodiments of the invention, reference will now be made to the appended drawings, which are not necessarily drawn to scale or proportion, and in which like reference numerals generally refer to like elements. The drawings are exemplary only, and should not be construed as limiting the invention.

FIGS. 2A-2B show two views of another tissue-sampling needle device embodiment;

FIG. 3 shows another tissue-sampling needle device embodiment; and

DETAILED DESCRIPTION

Figure 1A:
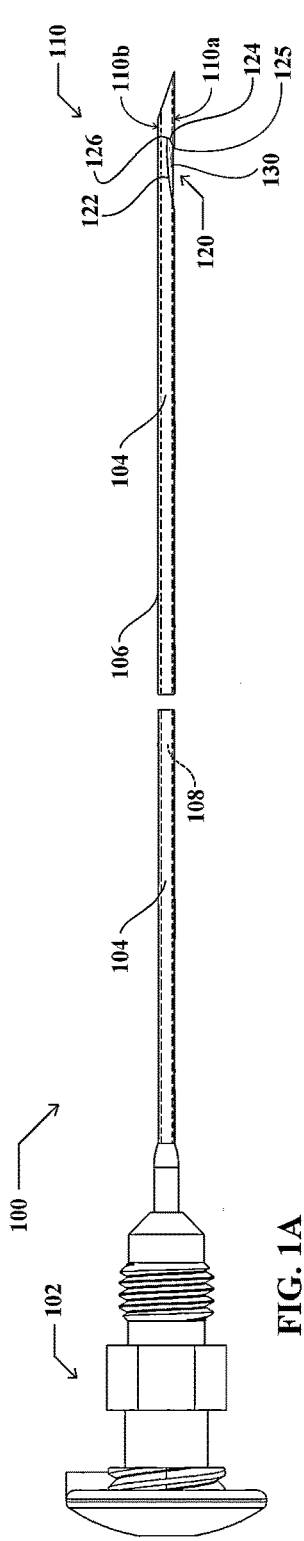
FIGS. 1A-1D show different views of a tissue-sampling needle device embodiment.
Figure 1B:
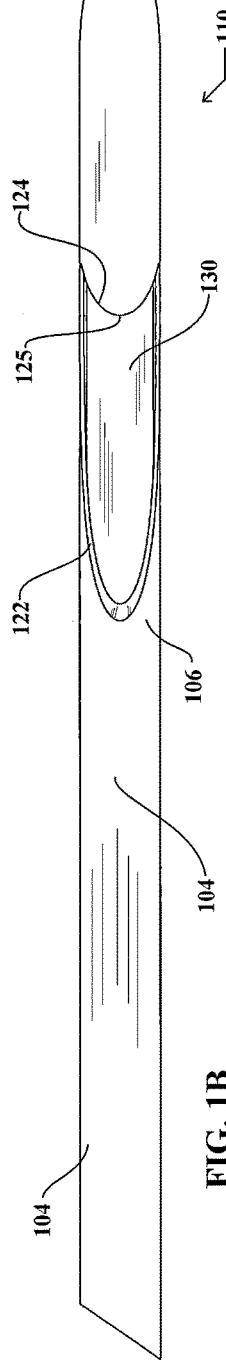

As used herein, the term "proximal" refers to the handle-end of a device held by a user, and the term "distal" refers to the opposite end. The term "surgical visualization device" refers to endoscopes including CCD, ultrasound, fiber optic, and CMOS devices, as well as other devices used for visualizing an internal portion of a patient body such as, for example, a laparoscope or bronchoscope.

One embodiment of a tissue-sampling needle device is described with reference to FIGS. 1A-1D, which show a tissue-sampling needle device 100. As shown in the side plan view of FIG. 1A, the device includes a proximal handle or hub 102 from which an elongate tubular cannula 104 extends distally. The cannula 104 includes a cannula wall 106 that defines a cannula lumen 108. A distal end 110 of the cannula 104 is beveled, including a long side 110a substantially parallel with the central longitudinal axis of the cannula 104 and extending to its distal-most tip end. A short side 110b of the beveled distal end 110 is opposite the long end 110a. A detailed illustration of the distal end 110 is shown in the top plan view of FIG. 1B. Other embodiments may include a double bevel, where one beveled surface is opposite the notch, or single or double bevels that are at least partially transverse relative to the notch.

Figure 1C:
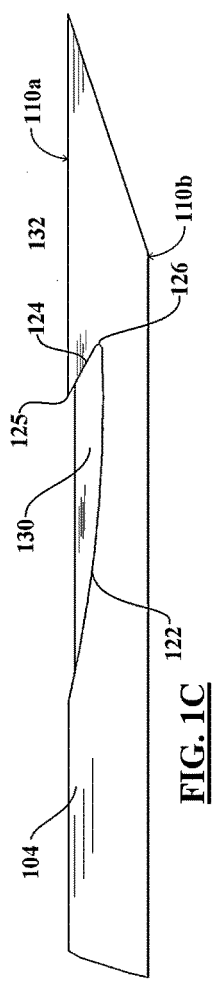
Figure 1D:
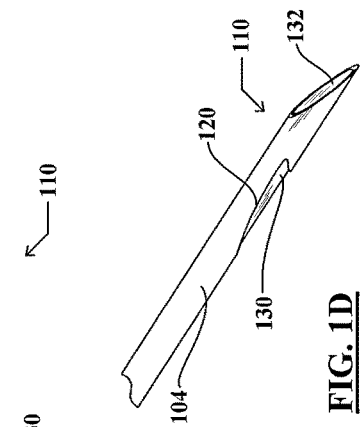

As shown in the side plan view of FIGS. 1A and 1C, and in the perspective view of FIG. 1D, a notch 120 is disposed proximally adjacent to the beveled distal cannula end 110 and is generally centered in longitudinal alignment with the long beveled end side 110a and opposite the short beveled end side 110b. In preferred embodiments, the notch 120 is generally arcuate, defined on its proximal side by a parabolic edge 122 extending along generally longitudinal, but somewhat curved lateral notch sides 124. The distal edge 124 of the notch 120 preferably is formed as generally parabolic lip that joins the proximal edge 122 at a pair of lip end portions 126 that preferably provide a curved transition between the proximal lateral and distal edges 122, 124. The radiused lip end portions 126 preferably are configured to provide stress relief within the cannula structure. A central distal lip portion 125 of the distal edge 124 preferably forms a proximal-facing cutting edge. In preferred embodiments, the notch will occupy about one-half the circumference of the cannula 104 at the broadest point of the notch. Inclusion of the bevel illustrated in FIG. 1C may provide advantages for successful sample collection. Specifically, contact of the bevel face against tissue may create a slight bias/pressure toward the notch that will help tissue to be pulled/captured into the notch when the stylet is withdrawn, including that contact pressure on the notch side of the shaft surface may be slightly greater than on the exterior surface immediately opposite the notch.

An elongate stylet 130 may be disposed removably through the cannula lumen 108. In preferred embodiments the stylet 130 will occupy substantially an entire cross-sectional area of at least a lengthwise portion of the cannula lumen 108. And, as shown in FIG. 1D, a distal end 132 of the stylet 130 will be beveled to align with the distal beveled cannula end 110 in a substantially coplanar manner. This construction will provide enhanced support for the cannula (particularly during navigation to a target site) including providing a generally solid cutting and/or tissue-penetrating distal tip end formed by the matching bevels of the stylet 130 and cannula 104. It should be appreciated that a rounded stylet end or other stylet end configuration may be practiced within the scope of the present invention. In certain embodiments, the distal beveled needle end may be closed, such that the lumen 108 extending longitudinally through the cannula terminates within the cannula 104. In these embodiments, a stylet may be reinserted into the needle lumen after the sample has been excised and captured through the notch into the needle lumen. In such a circumstance, the stylet may be extended distally to cover the open notch (thereby preventing contamination of the sample by inadvertent collection of cells along the needle track during withdrawal of the needle), but leaving room in a closed needle lumen portion for the sample to remain intact between the notch and a closed distal end in an embodiment where the needle lumen is closed at the distal end.

In one exemplary embodiment, the cannula 104 may be constructed as a 19-gauge needle made of 304 stainless steel, with an inner diameter of about 0.9 mm (about 0.037 inches). In this embodiment, the notch 120 may be circumferentially located opposite and proximal of a distal bevel that is at about a 30° angle relative to the short side such that a proximal-most end of the notch 120 (defined by the proximal edge 122) is about 9 mm (about 0.36 inches) longitudinally proximal of the distal-most tip end of the cannula 104. In this embodiment, the longitudinal distance between the proximal-most notch edge 122 and the proximal-most portion of the distal lip 125 will be about 4 mm (about 0.16 inches). The proximal-most portion of the distal lip 125 will be about 0.6 mm (about 0.025 inches) from the distal-most end of the notch 120, which will be defined by a curved lip end portion 126, including a radius of curvature of about 0.05 mm (0.002 inches), joining the distal edge 124 with the proximal edge 122. The longitudinal linear distance between the distal-most lip end portions 126 and the proximal end of the bevel 110 opposite the notch 120 may be about 1.47 mm (0.058 inches) in 19-gauge, 20-gauge, 21-gauge, or 22-gauge embodiments to provide optimal strength and notch position relative to the needle's distal end. The 19-gauge needle may be used with a sheath measuring about 4.2 to 5.2 Fr. A beveled NiTi stylet 130 may be disposed slidably/removably through the cannula lumen. It should be appreciated that, while a needle not larger than a 19-gauge needle is preferred, smaller gauge needles such as—for example—22-gauge and 25-gauge needles may be practiced within the scope of the present invention (although, it will be appreciated that their absolute dimensions will vary from those disclosed here for the 19-gauge example).

FIGS. 2A, 2B and 3 show additional embodiments of a tissue-sampling needle device 200. As shown in the side plan view of FIG. 2A, the device includes a proximal handle or hub 202 from which an elongate tubular cannula 204 extends distally. The cannula 204 includes a cannula wall that defines a cannula lumen. A distal end 210 of the cannula 204 is beveled, including a long side 210a substantially parallel with the central longitudinal axis of the cannula 204 and extending to its distal-most tip end. A short side 210b of the beveled distal end 210 is opposite the long end 210a. A detail view of the needle device 200 is shown in a top plan view in FIG. 2B. The distal end 210 may be open to the lumen or may be closed. In embodiments with an open end 210, a sample may be ejected out the distal end after collection.

As shown in the side views of FIGS. 2A and 3, a notch 220 is disposed proximally adjacent to the beveled distal cannula end 210 and is generally centered in longitudinal alignment with the long beveled end side 210a and opposite the short beveled end side 210b. In preferred embodiments, the notch 220 is generally arcuate, defined on its proximal side by a parabolic edge 222 extending along generally longitudinal, but somewhat curved lateral notch sides 224. The distal edge 224 of the notch 220 preferably is formed as generally parabolic lip that joins the proximal edge 222 at a pair of lip end portions 226 that preferably provide a curved transition between the proximal and distal edges 222, 224. A central distal lip portion 225 of the distal edge 224 preferably forms a proximal-facing cutting edge. In preferred embodiments, the notch will occupy about one-half the circumference of the cannula 204 at the broadest point of the notch.

As shown in FIG. 2A, the cannula 204 includes surface features 240 configured to enhance echogenicity, thereby providing an improved ability to navigate the device during an EUS procedure. The surface features 240 are shown here as dimples on an exterior surface of the cannula 204, but may alternatively be embodied as grooves or other regular or irregular features on an external or internal surface. Embedded echogenic features such as bubbles, voids, or pieces of echo-contrasting materials may also be used within the scope of the present invention. Those of skill in the art will appreciate that many currently-known and/or future-developed echogenicity-enhancing means may be used within the scope of the present invention. As used herein, the terms echogenic and echogenicity-enhancing are used to refer to structural features that increase the reflectivity of ultrasound waves used during ultrasound visualization of a device, with the increase being over the typical ultrasound reflectivity/visualizability of a device lacking the features described.

FIG. 3 is similar to FIG. 2A, but shows that the echogenic features 240 may extend distally across the space occupied by the notch 220. It is preferable that echogenicity-enhancing features be disposed at a specified predetermined distance from the distal-most tip end of the cannula 204. Although the echogenic features 240 are shown at a distance from the notch 220, a cannula according to the present embodiments may be constructed with those echogenic features disposed flush up to the margins of the notch. A stylet 230, which may include echogenicity-enhancing features may be disposed through the cannula lumen of the embodiments of FIGS. 2A-3.

Figure 4A:
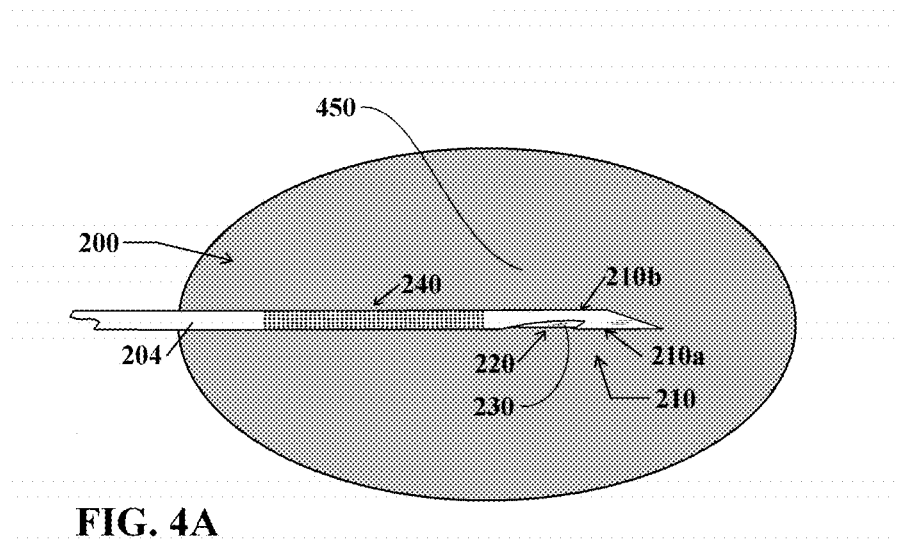
FIGS. 4A-4C show a method of using a tissue-sampling needle device embodiment.
Figure 4B:
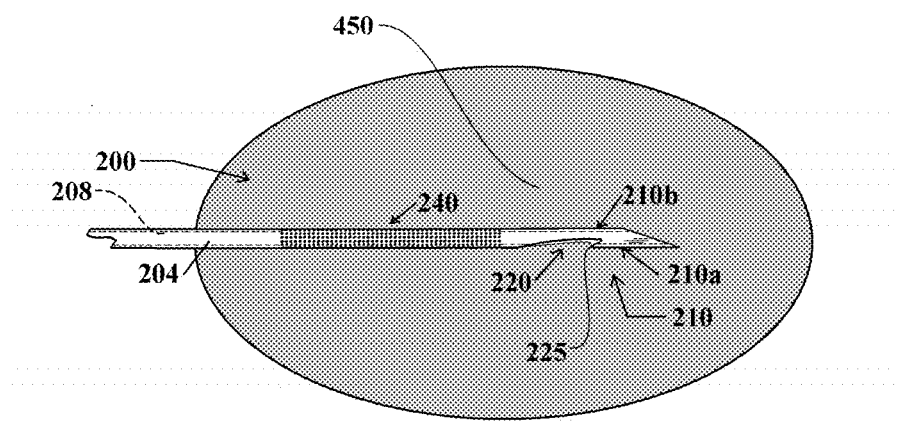
Figure 4C:
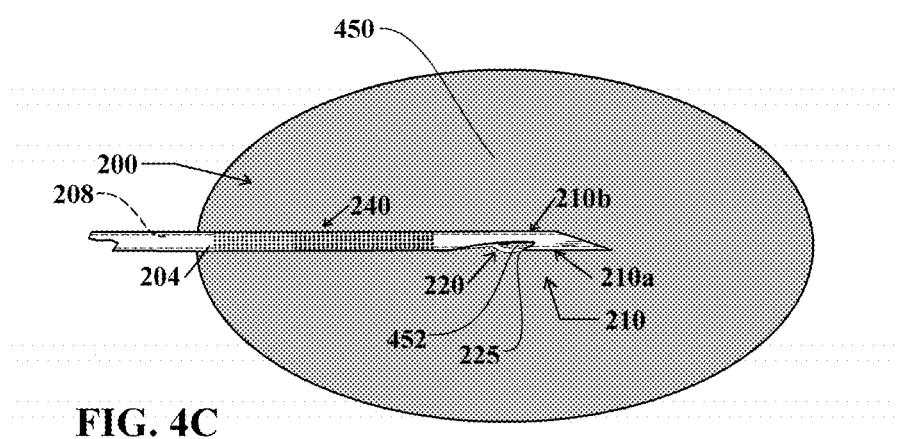

A method of tissue collection is described with reference to FIGS. 4A-4C, using the needle device 200 of FIGS. 2A-2B. First, as shown in FIG. 4A, the needle cannula 204, with the stylet 230 disposed therein, is directed into a target site 450 to be sampled (e.g., a tumor mass). Next, as shown in FIG. 4B, the stylet 230 is withdrawn and suction is applied to the proximal end of the needle cannula lumen 208. This will pull tissue from the target site 450 through the notch 220 into the lumen 208. As shown in FIG. 4C, the user will then quickly retract the cannula 204 proximally such that the proximal-facing cutting edge of the distal notch's central lip 225 cuts a sample 452 of tissue from the target site that is drawn into the lumen 208 and that may be captured within, distal, or proximal of the notch 220. The cannula 204 may be advanced and retracted slightly (e.g., about half a centimeter, two or three times) and/or rotated or otherwise manipulated by the user if desired to try to capture sample material. The cannula 204 may be bowed slightly during use to accentuate contact of the notch 220 with adjacent tissue to promote improved sample collection.

The sample obtained preferably will include a desirable number of intact cells, preferably more intact cells than are ordinarily obtained using a non-notched FNA biopsy needle ("more" indicating both a greater number and a higher degree of cell integrity within the sample obtained). It has been found that histological-grade FNB samples may be obtained in this manner, which may be preferred for certain diagnostic purposes over the cytological-grade samples typically obtained through FNA. The needle may then be withdrawn from the patient's body.

In one preferred embodiment, during introduction of the device into a patient body, the cannula 204 will be directed through the working channel of a peroral endoscope such as a duodenoscope into a patient's body. It is then navigated (under ultrasound visualization if echogenicity-enhancing features are provided, as in the embodiment shown in FIGS. 2A-3) into the target site 450. In other embodiments, the device 200 may be introduced through other access means known in the art including percutaneous means such as direct insertion of the needle cannula through a patient's skin or insertion through a trocar, sheath, or other access device (with or without endoscopic or ultrasound visualization), all within the scope of the present invention. It should also be appreciated that an outer sheath may be disposed slidably along the exterior of the cannula 204 and advanced over the notch 220 after the sample is excised by the cutting edge. This configuration, which may be practiced within the scope of the present invention, may lessen the likelihood that the sample collected will become lost or contaminated during needle withdrawal.

The needle device and methods disclosed here provide the advantages associated with FNA needles of small size and maneuverability, while offering a means of collecting more intact samples from target sites. They also are not hampered by the guillotine-style moving parts of other notched needle systems known in the biopsy art (which are generally larger in scale due to a need for having a cutting member that movably transects the notch).

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:
1. A tissue-sampling needle device, comprising:
   an elongate tubular cannula including a cannula wall defining a longitudinal cannula lumen constructed to receive a tissue sample;
   a distal beveled end of the cannula including a long side and a short side;
   a notch through the cannula wall, open to the cannula lumen and configured to collect a tissue core sample;
   where the notch is disposed proximally of, and adjacent to, the beveled distal cannula end and is generally centered radially opposite the short beveled end side;
   where a distal end of the notch includes a generally parabolic distal lip defined by a portion of the cannula wall, including a proximal-facing cutting edge that extends proximally from a distal-most end of the notch such that a central distal lip portion including the cutting edge is disposed more proximally than lip end portions
      that transition directly, at an acute angle relative to a longitudinal central axis, from the central lip portion to, and
      that are continuous with,
   generally longitudinal lateral sides of the notch, which join together to form a parabolic proximal end of the notch;
   where the parabolic proximal end of the notch and the generally parabolic distal lip are joined by a pair of radiused transition curves forming the lip end portions between the generally longitudinal lateral sides;

where the cannula proximal of, across, and distal of the notch, including the cutting edge, includes a uniform outer diameter;
where the cannula lumen lacks any inner cutting member for movably transecting the notch; and
wherein the cannula is configured as sufficiently flexible and sufficiently long for passage through a working channel of a peroral surgical visualization device to a duodenum of a patient.

2. The device of claim 1, wherein the cannula comprises a 19-gauge needle including an inner diameter of about 0.9 mm (about 0.037 inches), wherein the notch occupies about one-half of an outer circumference of the cannula.

3. The device of claim 1, further comprising a solid stylet disposed through, and occupying substantially an entire cross-sectional area of, at least a lengthwise portion of the cannula lumen, where the solid stylet completely occludes the lumen and the notch in a first operational state of the device.

4. The device of claim 3, where a distal end of the stylet is beveled to align with the distal beveled cannula end in a substantially coplanar manner.

5. The device of claim 3, where a distal end of the stylet is rounded.

6. The device of claim 1, further comprising a pattern of echogenic surface features disposed immediately adjacent to and proximal of the notch.

7. The device of claim 6, wherein the echogenic surface features comprise dimples in the cannula wall.

8. The device of claim 1, further comprising a solid stylet disposed removably through, and occupying substantially an entire cross-sectional area of and an entire length of the cannula lumen without extending substantially beyond a distalmost end terminus of the cannula, such that the solid stylet completely occludes the lumen and the notch.

9. The device of claim 1, wherein the cannula comprises a selected one of a 19-gauge needle, 22-gauge needle, or 25-gauge needle, wherein the notch occupies about one-half of an outer circumference of the cannula.

10. The device of claim 1, where the distal beveled end of the cannula is open to the cannula lumen.

11. The device of claim 1, comprising a consistent inner diameter of the cannula along an entire length of the cannula lumen, including across the notch.

12. A notched aspiration biopsy needle, comprising:
a flexible elongate tubular cannula sized no larger than 19-gauge, including a cannula wall defining a cannula lumen configured to communicate with a proximal source of suction;
wherein the cannula lumen extends longitudinally through the cannula;
a distal beveled end of the cannula including a long side and a short side;
a notch through the cannula wall, open to the cannula lumen and configured to collect a tissue core sample;
wherein the notch is disposed proximally adjacent to the beveled distal cannula end and is generally centered in longitudinal alignment with the long beveled end side and opposite the short beveled end side;
wherein the notch includes a cutting edge defined by a proximal-facing portion of the cannula wall, where the cutting edge is both longitudinally and radially arcuate such that a center-most portion of the cutting edge
is more proximally disposed than are lateral-end portions of the cutting edge; and
is nearer to a distal-most open portion of the notch than to a proximal-most portion of the notch,
where said proximal-most portion of the notch is parabolic, and the proximal-facing edge of the notch transitions from the cutting edge directly, at an acute angle relative to a longitudinal central axis, to and through a pair of radiused lip-ends to the parabolic proximal-most portion of the notch, where the radiused lip-ends have a radius of curvature equal to about one-eightieth of a distance between a proximal-most end of the notch and a proximal-most edge of the cutting edge; and
wherein the cannula is configured as sufficiently flexible and sufficiently long for passage through a working channel of a peroral surgical visualization device to a duodenum of a patient.

13. The needle of claim 12, further comprising a stylet disposed through, and occupying substantially an entire cross-sectional area of, at least a lengthwise portion of the cannula lumen, wherein a distal end of the stylet is rounded and a lateral side of the stylet fully obscures the notch when the distal end of stylet is distal of the notch.

14. A method of tissue collection comprising the steps of:
providing a tissue-sampling needle device comprising:
an elongate tubular cannula including a cannula wall defining a longitudinal cannula lumen constructed to receive a tissue sample;
a distal beveled end of the cannula including a long side and a short side:
a notch through the cannula wall, open to the cannula lumen and configured to collect a tissue core sample;
where the notch is disposed proximally of, and adjacent to, the beveled distal cannula end and is generally centered radially opposite the short beveled end side;
where a distal end of the notch includes a generally parabolic distal lip defined by a portion of the cannula wall, including a proximal-facing cutting edge that extends proximally from a distal-most end of the notch such that a central distal lip portion including the cutting edge is disposed more proximally than lip end portions
that transition directly, at an acute angle relative to a longitudinal central axis, from the central lip portion to, and
that are continuous with,
generally longitudinal lateral sides of the notch, which join together to form a parabolic proximal end of the notch;
where the parabolic proximal end of the notch and the generally parabolic distal lip are joined by a pair of radiused transition curves forming the lip end portions between the generally longitudinal lateral sides;
where the cannula proximal of, across, and distal of the notch, including the cutting edge, includes a uniform outer diameter; and
where the cannula lumen lacks any inner cutting member for movably transecting the notch;
directing the distal beveled end of the cannula into a target site;
applying suction to the needle lumen in a manner drawing tissue into the needle lumen through the notch; and
moving the needle proximally in a manner engaging the proximally-facing cutting edge with the target site such that an intact tissue core sample from the target site is collected into the needle lumen.

15. The method of claim 14, wherein the step of providing the tissue-sampling needle device further comprises providing a stylet disposed through the lumen, and further comprising a step of completely proximally withdrawing the stylet before moving the needle proximally in a manner engaging the proximally-facing cutting edge with the target site.

16. The method of claim 14, further comprising a step of obtaining a histological grade fine needle biopsy sample from the target site and conducting histological analysis of the sample.

17. The method of claim 14, where the step of directing the distal beveled end of the cannula into a target site comprises directing the distal beveled end through a peroral endoscope.

\* \* \* \* \*